United States Patent
Bödicker et al.

(10) Patent No.: US 7,050,611 B2
(45) Date of Patent: May 23, 2006

(54) METHOD AND COMPUTER SYSTEM FOR SCREENING OF MEDICAL CASES

(75) Inventors: Anke Bödicker, Bremen (DE); Dietmar Dechow, Bremen (DE)

(73) Assignee: Mevis Breastcare GmbH Co. KG, Bremen (DE)

( * ) Notice: Subject to any disclaimer, the term of this patent is extended or adjusted under 35 U.S.C. 154(b) by 678 days.

(21) Appl. No.: 09/870,386

(22) Filed: May 29, 2001

(65) Prior Publication Data
US 2002/0193676 A1  Dec. 19, 2002

(51) Int. Cl.
*G06K 9/00* (2006.01)

(52) U.S. Cl. ................................ 382/128
(58) Field of Classification Search ............ 382/128, 382/130; 345/810, 763; 715/783, 762, 835–837
See application file for complete search history.

(56) References Cited

U.S. PATENT DOCUMENTS

| | | | |
|---|---|---|---|
| 4,807,110 A | 2/1989 | Pomerene et al. | |
| 5,452,416 A * | 9/1995 | Hilton et al. | 715/783 |
| 5,623,592 A | 4/1997 | Carlson et al. | |
| 5,867,163 A | 2/1999 | Kurtenbach | |
| 5,917,929 A | 6/1999 | Marshall et al. | |
| 5,987,345 A | 11/1999 | Engelmann et al. | |
| 6,041,135 A | 3/2000 | Buytaert et al. | |
| 6,097,389 A * | 8/2000 | Morris et al. | 715/804 |
| 6,098,064 A | 8/2000 | Pirolli et al. | |
| 6,127,669 A | 10/2000 | Sidiropoulos et al. | |
| 6,151,662 A | 11/2000 | Christie et al. | |
| 6,154,767 A | 11/2000 | Altschuler et al. | |
| 6,154,826 A | 11/2000 | Wulf et al. | |
| 6,269,379 B1 * | 7/2001 | Hiyama et al. | 707/104.1 |
| 6,904,161 B1 * | 6/2005 | Becker et al. | 382/128 |

FOREIGN PATENT DOCUMENTS

WO   WO 96/31829 A   10/1996

OTHER PUBLICATIONS

Courter et al, "Mastering Microsoft Office 2000 Professional Edition", Copyrighted 1999, ISBN 0-7821-2313-9.*

* cited by examiner

*Primary Examiner*—Jose L. Couso
*Assistant Examiner*—Tom Y. Lu
(74) *Attorney, Agent, or Firm*—Martin Fleit; Paul D. Bianco; Fleit Kain Gibbons Gutman Bongini & Bianco (57) ABSTRACT

A method and computer system for screening of medical cases in which the computer system has a user interface which enables pre-programming of a sequence of images to be reviewed for each of a group of medical cases. The pre-programming is conducted by means of symbols or icons which are selectable by a user. The pre-programming of the sequence of images is done in a configuration phase of the computer system. During the screening procedure, the user can go from one image to the next by performing a single action input operation, such as, making a mouse click or pressing a next-step button. This has the advantage that the user can fully concentrate on reviewing the medical images without distraction.

19 Claims, 9 Drawing Sheets

MODE 1

MODE 2

MODE 3

METHOD AND COMPUTER SYSTEM FOR SCREENING OF MEDICAL CASES

CROSS REFERENCES TO RELATED APPLICATION

This application is related to the following patent applications, filed on the same day as this application and assigned to the same assignee, MeVis Technology GmbH & Co. KG
(1) A Method And Computer System For Prefetching Of Images, Ser. No. 09/870,389; filed May 29, 2001,
(2) A Method And System For In-Service Monitoring And Training For A Radiologic Workstation, Ser. No. 09/870,388; filed May 29, 2001,
which are hereby incorporated by reference to be understood in connection with the present invention.

FIELD OF THE INVENTION

The present invention relates to the field of screening of medical cases, and more specifically to a method, apparatus and computer system, which has a user interface to facilitate the screening.

BACKGROUND AND RELATED ART

In a medical screening procedure, such as radiologic screening mammography, a large number of medical images need to be reviewed. In order to allow a radiologist to fully concentrate on the review of the medical images an efficient and user friendly interface is required.

U.S. Pat. No. 5,917,929 shows a user interface for a computer aided diagnosis system. A touch sensitive display screen is provided to display status information and to receive instruction from an operator. The display screen displays miniature images of the films having colour-coded borders so that the operator monitors the processing of the radiologic films. The interface includes view selection buttons to allow the operator to select certain x-ray images. This interface requires that the user select the images and the view of the images during the ongoing screening procedure.

U.S. Pat. No. 5,987,345 shows a method and system for displaying of medical images and computer output from various computer aided diagnosis (CAD) schemes on the images. Images are loaded into the display system and displayed in a main viewing area. Individual abnormality from CAD schemes can be viewed by clicking buttons with minified (postage stamp size) images with CAD annotation rendered into them. The images and results are then shown on a high-speed monitor. Again this prior art system is deficient or has disadvantages as the complexity of the user interface requires a substantial amount of the radiologist's attention and concentration during the screening.

SUMMARY OF THE INVENTION

It is an object of the present invention to provide a novel method and system for screening of medical cases.

It is another object of the present invention to provide a method and a computer system for screening of medical cases with a user interface which allows the radiologist to focus his or her attention to the review of the medical cases without distraction of attention due to the complexity of the user interface.

These and other objects and advantages of the invention are achieved by a method and a system that utilizes a user interface enabling a user to pre-program a typical sequence of images to be reviewed in the workflow of the screening procedure of a number of medical cases. The pre-programming is advantageously achieved by means of symbols or icons being provided by a graphical user interface.

An individual icon can specify a certain view and/or a certain image processing algorithm to be performed, activate the marking of a region of interest (ROI) or the entering of a diagnosis/annotation, or activate the display of computer assisted diagnosis (CAD) markers. The user can select an icon by clicking on it and by moving the icon to a sequence bar by means of a drag-and-drop operation. This way a sequence of icons results that specifies the sequence of images to be rendered, including images for prompting a user action, images for inputting an annotation and/or another sequence of actions, and images resulting from an image processing operation to be performed for the screening of an individual medical case. In the following the term "image" is used for all kinds of images, including raw data mammograms, views of images, images resulting from image processing operations, image processing and other operations and user operations, prompts for user actions and other screens for the purposes of workflow management.

After the pre-programming of the sequence has been done by the user, the user can start the screening process. Typically a stack of medical cases is assigned to the user for review. As the sequence of images to be rendered for an individual medical case is pre-programmed the user can go from one image, such as a view or an operation, to the next by performing a single action input operation, such as a mouse click, pressing on a "next-step" button, touching an area of a touch-screen or by natural language, if speech recognition is available.

When the sequence of images of the first case to be reviewed has been completed the control goes to the consecutive medical case and restarts the same sequence. This way the user can go through all images to be reviewed by just performing single action input operations for going from one image to the next. This has the advantage that the user can focus his or her attention to the review of the medical cases without being distracted by a complex user interface requiring frequent decision making as regards the control of the display of the images.

Preferably the user has to do the pre-programming only once. The pre-programmed sequence can be stored in conjunction with the user's profile. When the user logs on, the pre-programmed sequence is retrieved and re-activated. Further, it is possible for the user to edit the pre-programmed sequence in order to modify the sequence.

Another advantageous aspect of the invention is that the throughput of a radiologic workstation can be optimised in two ways. First, this is due to the fact that the time required for the review of an individual medical case is minimised by the user interface of the invention. Second, the computer system can anticipate the next user interaction, thus shortening the system response time. In particular this enables prefetching of consecutive images into the image cache as it is disclosed in co-pending U.S. Patent Application (1) entitled "A Method And Computer System For Prefetching Of Images", filed May 29, 2001, here incorporated by reference.

However if the radiologist needs to perform actions during the screening procedure, which are not contained in the pre-programmed sequence, this can be done by means of a keypad and/or keyboard. The specific action can be, for example, a particular image processing algorithm, a particular view, entering of an annotation or a diagnosis, marking of regions of interest or the like. After the radiologist has completed the special operations, which have not been pre-programmed, he or she can return to the pre-programmed sequence by simply resuming to perform the single action input operations.

BRIEF DESCRIPTION OF THE DRAWINGS

A more complete appreciation of the invention and many of the attendant advantages thereof will be readily apparent from the following detailed description of preferred embodiments of the invention when considered in connection with the accompanying drawings, wherein.

DESCRIPTION OF THE PREFERRED EMBODIMENTS

Figure 1:
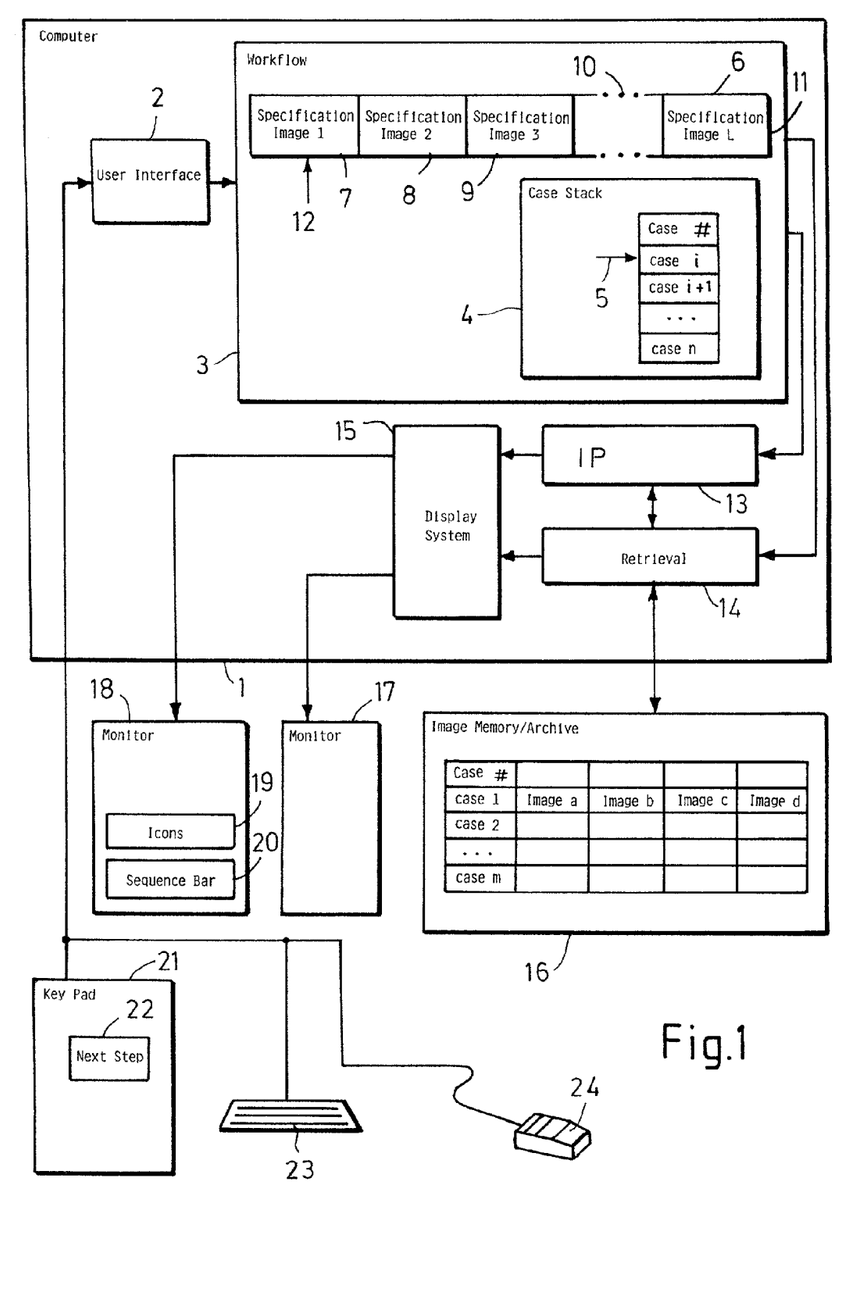
FIG. 1 is a block diagram of an embodiment of the computer system according to the invention.

Referring now to the drawings, in particular FIG. 1, a preferred embodiment of the invention will be described.

FIG. 1 shows a block diagram of the computer system according to the invention. The computer system has a computer 1 comprising a graphical user interface 2. The graphical user interface 2 is coupled to a workflow memory 3. The workflow memory 3 has a stack 4 for storing a stack of cases to be reviewed in the screening procedure. In the example considered here the cases case i, case i+1, ... case n are contained in the stack 4 in this order. Each of the cases has a unique identifier ("case ID").

The current case to be reviewed is identified by a pointer 5. At the time considered in the example of FIG. 1 the pointer 5 is directed to the first case i in the stack 4.

The workflow memory 3 has a memory 6. The memory 6 has a number of L data fields of which data fields 7, 8, 9, 10 and 11 are shown in FIG. 1. Each of the data fields stores a specification of an image reviewed of each of the cases. The current image in the sequence is identified by a pointer 12 which points to the current image, in the example considered here, image 1 of the sequence.

The workflow memory is coupled to an image processing (IP) module 13 and to retrieval module 14. The IP module 13 is also coupled to the retrieval module 14 for retrieval of image data on which an image processing operation, such as a computer aided diagnosis (CAD) operation, is to be performed. Both the IP module 13 and the retrieval module 14 have an output which is coupled to display system 15.

Further the computer system of FIG. 1 has a database 16 that is coupled to the retrieval module 14. The database 16 can be part of the computer 1 or it can be an external database as in the example depicted in FIG. 1. The database 16 contains an image memory and/or archive for a number of cases 1 to m. In the example considered here each of the medical cases comprises a number of 4 images: image a, image b, image c, and image d.

For example, in mammography each breast is usually imaged twice. The first image being a top view ordinarily called the craniocaudal view ("CC") and the second image being a lateral view ordinarily called the mediolateral oblique view ("MLO"). Therefore, for applications of the computer system of FIG. 1 for screening mammography, the images of a medical case of the database 16 can be a right MLO image (image a), a left MLO image (image b), a right CC image (image c), and a left CC image (image d). Ordinarily each of the individual cases forming part of the screening program is structured in the same way as explained above.

Further the computer system has a monitor 17 and a monitor 18. The monitor 17 and the monitor 18 are coupled to the display system 15. The icons 19 which belong to the graphical user interface 2 are displayed on the monitor 18 and/or 17. Further a sequence bar 20 is displayed on the monitor 18 enabling the user to pre-program the sequence of images by drag-and-drop of icons 19 onto the sequence bar 20.

Further, the user interface 2 is coupled to a keypad 21 having a next-step button 22. By pressing the next-step button 22, the user goes from the current image to a consecutive image. In other words, when the user operates the next-step button 22 the pointer 12 is shifted to the next consecutive data field of the memory 6, such that the next consecutive image is retrieved and/or generated for display on one of the monitors 17 and/or 18.

Further, the user interface 2 is coupled to a keyboard 23 and to a mouse 24.

To prepare the screening of the cases, the computer system first needs to be initialised by loading the cases to be reviewed into the stack 4. The pointer 5 is set to the first case—case i—of the stack 4. For the pre-programming of the sequence of images the user sequentially selects a number of icons 19 and performs drag-and-drop operations to move selected icons to the sequence bar 20.

An individual icon 19 can be selected on the monitor 18 by clicking on the icon 19 by means of the mouse 24 and moving the icon to the sequence bar 20 by making a corresponding move of the mouse 24. Each of the icons 19 can be selected several times for the pre-programming.

When the sequence of icons in the sequence bar 20 is complete the user performs an enter operation by pressing the enter button of the keyboard 23 or clicking on an ok button or the like. This way the sequence of icons of the sequence bar 20 is transformed into data contained in the data fields 7 to 11 of the memory 6. In other words, each of the icons 19 which have been selected by the user specifies a particular image in the sequence of images to be rendered for each individual case. The pointer 12 is set to the first element of the sequence of images contained in the data field 7.

After the initialisation of the computer system the screening procedure can start. The first image 1 of the sequence of images of case i is displayed in accordance with the specification stored in the data field 7. For example the data field 7 can specify a right craniocaudal image with a contrast limited adaptive histogram equalisation (CLAHE). To display the first image 1 a request is made to the retrieval module 14 in order to retrieve the left craniocaudal image of the case i. The retrieval is made with the case ID of case i as a key to perform the database access of database 16.

When the corresponding image data is available the IP module 13 performs a CLAHE operation on the image data and outputs the result to the display system 15 for display on monitor 17 or 18.

After the radiologist has reviewed image 1 he or she presses the next-step button in order to go to the next image in the sequence—which is the image 2. When the radiologist presses the next-step button 22 the pointer 12 is shifted to the data field 8 containing the specification for the image 2.

The image data corresponding to the specification contained in the data field 8 is retrieved and/or generated by the computer system and the image 2 is displayed on monitor 17 or 18. By repeatedly pressing the next-step button 22 the user of the computer system can go through an entire medical case in accordance with the pre-programmed sequence stored in the memory 6. When the pointer 12 is at the last data field 11 pressing the next-step button 22 will move the pointer 5 to the next case "case i+1" and the pointer 12 is reset to the initial position of data field 7. This way the complete display sequence is repeated for the next case i+1 without a requirement for a user action other than pressing the next-step button 22.

Figure 2:
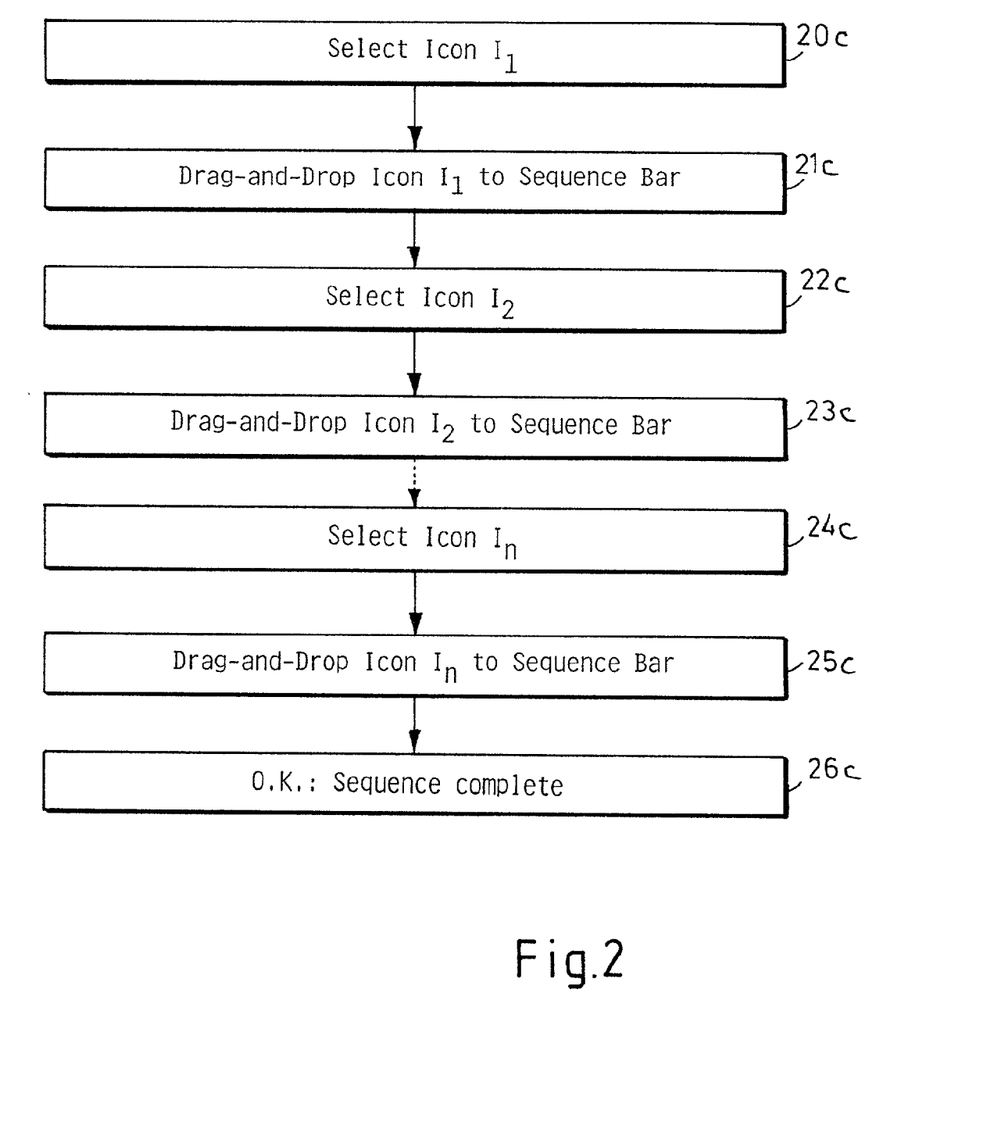
FIG. 2 is a flow chart illustrating the pre-programming of the sequence of images to be reviewed for a medical case.

FIG. 2 shows the sequence of steps performed by a user in the configuration phase of the computer system for the pre-programming of the sequence of images to be reviewed for each individual case of the screening program. In step 20c the user selects an icon $I_1$ corresponding to a particular image specification. This icon is moved to the sequence bar by a drag- and-drop operation in step 21c.

Corresponding steps 22c and 23c are performed with respect to the same or another icon $I_2$ until the last icon $I_n$ is selected in step 24c and moved to the sequence bar in step 25c. To complete the pre-programming of the sequence of images the user performs an enter operation in step 26c.

Figure 3:
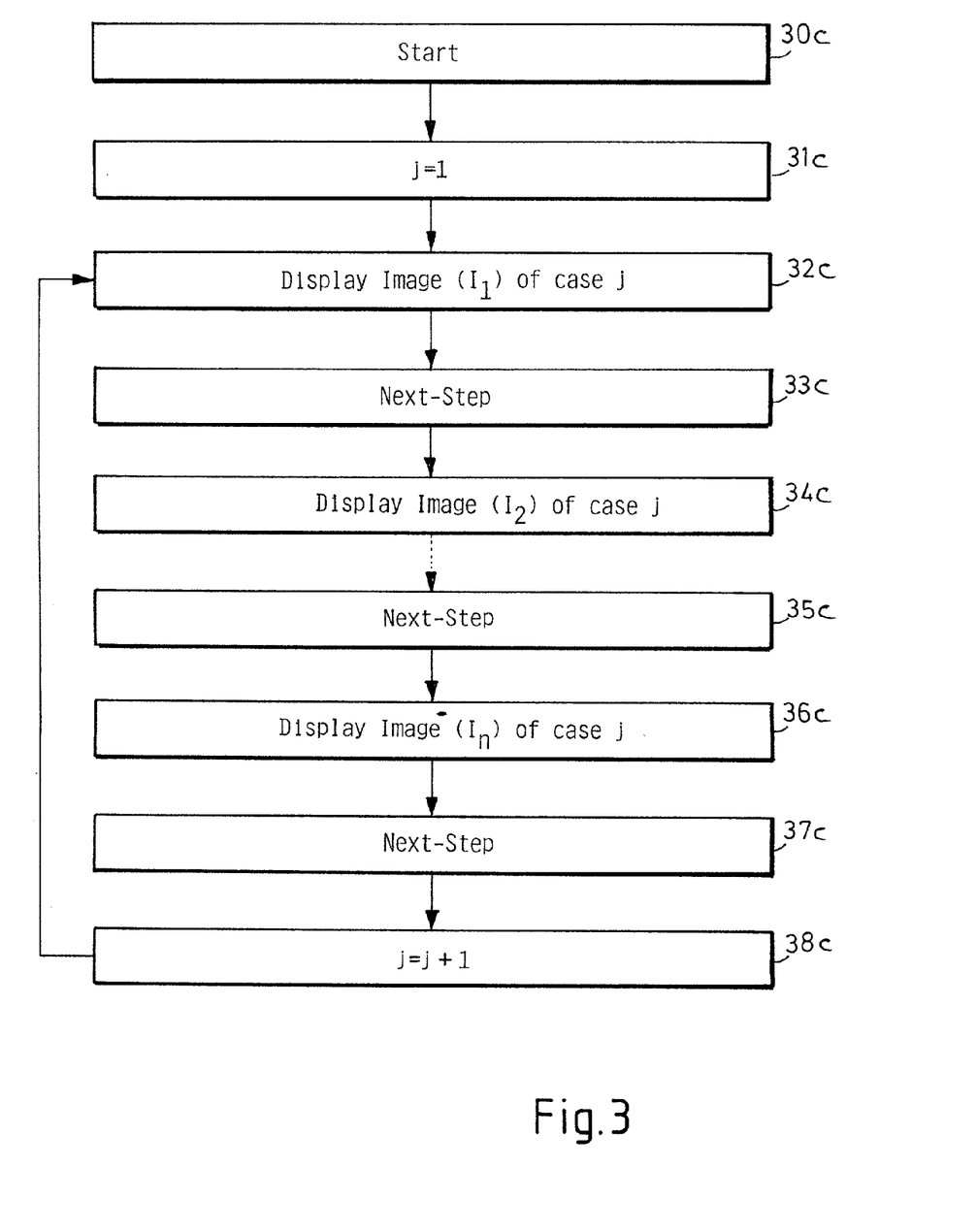
FIG. 3 is a flow chart illustrating the screening procedure relying on the pre-programmed sequence.

FIG. 3 illustrates the operation of the computer system of FIG. 1 after the configuration phase. In order to start the screening procedure the user presses a start button in step 30c.

In step 31c the variable j is initialised to be equal to 1. In step 32c the first image of the sequence is retrieved and/or generated in accordance with the specification provided by the first icon $I_1$ of the sequence of icons of the sequence bar. After review of the first image, which is displayed for the current case, the user presses the next-step button in step 33c such that the consecutive image in the sequence is displayed in accordance with the specification provided by the consecutive icon $I_2$ of the sequence of icons of the sequence bar 20.

After the display of this image in step 34c the procedure continues by repetitively pressing the next-step button (steps 35c, 36c) until the last image in the sequence of the current case j=1 is reached.

When the next-step button is pressed in step 37c after the display of the last image for the current case in step 36c, the variable j is incremented and the control goes back to step 32c in order to repeat the steps 32c to 38c with respect to the consecutive case of the case stack 4. By incrementing the variable j the corresponding pointer (cf. pointer 5 of FIG. 1) is shifted to the consecutive case.

It is to be noted that other actions other than displaying of images (steps 32c, 34c . . . 36c) can be performed in the operation of the computer system such as making a diagnosis, marking of a region in the image, entering an annotation, performing an image processing operation and/or entering a diagnosis or other actions—depending on the particular pre-programmed sequence. Also the use or activity can always deviate from the pre-programmed sequence by directly inputting, requesting and/or performing an action by means of the key pad, key board, touch screen or by voice control.

Figure 4:
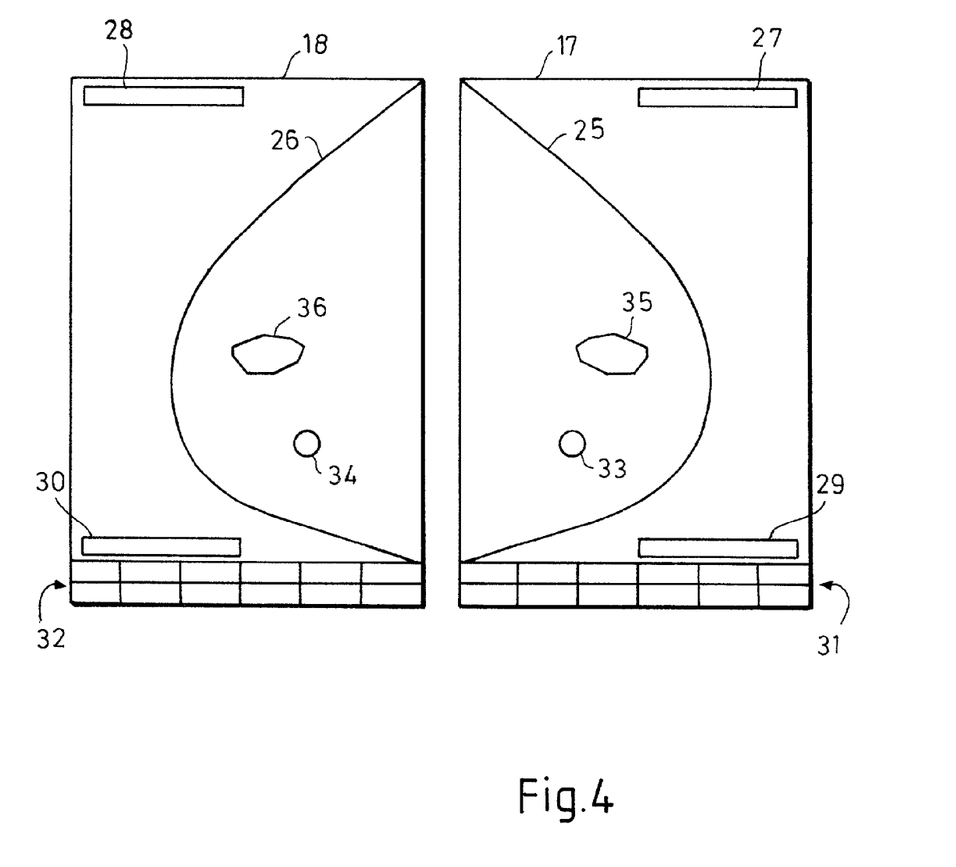
FIG. 4 shows an embodiment of a graphical user interface according to the invention.

FIG. 4 shows an example for the display and screen layout of the monitors 17 and 18 of the computer system of FIG. 1. The right monitor 17 shows a mammogram 25; the left monitor 18 shows a mammogram 26. The display fields 27 and 28 show CAD status information for the mammograms 25 and 26, respectively. The display fields 29 and 30 show image type information for the mammograms 25 and 26, respectively, including image enhancement status information, if any.

Further, on the right monitor 17 there is a toolbar 31 having a number of buttons or icons. Each of the buttons or icons of the tool bar 31 corresponds to a particular selection of a tool, such as image magnification, CLAHE or wavelet enhancement.

A corresponding tool bar 32 is displayed on the left monitor 18 for specifying particular views of images. In the configuration phase of the computer system the user can pre-program the sequence of images to be displayed for each individual case by drag-and-drop of the icons of the toolbars 31 and 32 to the sequence bar 20.

Alternatively the pre-programming can also be performed without a drag-and-drop operation, for example, by sequentially selecting the buttons of the tool bars 31 and/or 32. As a further alternative, the tool bars 31 and 32 can also be implemented by means of pop-up or pull-down menus. During the screening operation the user can still directly use the icons or buttons to divert from the pre-programmed workflow sequence.

In the example considered here the user has utilised an ellipse contour tool provided by the tool bar 31 in order to highlight the regions 33 and 34 of the mammograms 25 and 26, respectively. Likewise the user has utilised the freehand contour tool to highlight the regions 35 and 36 of the mammograms 25 and 26 respectively.

Figure 5:
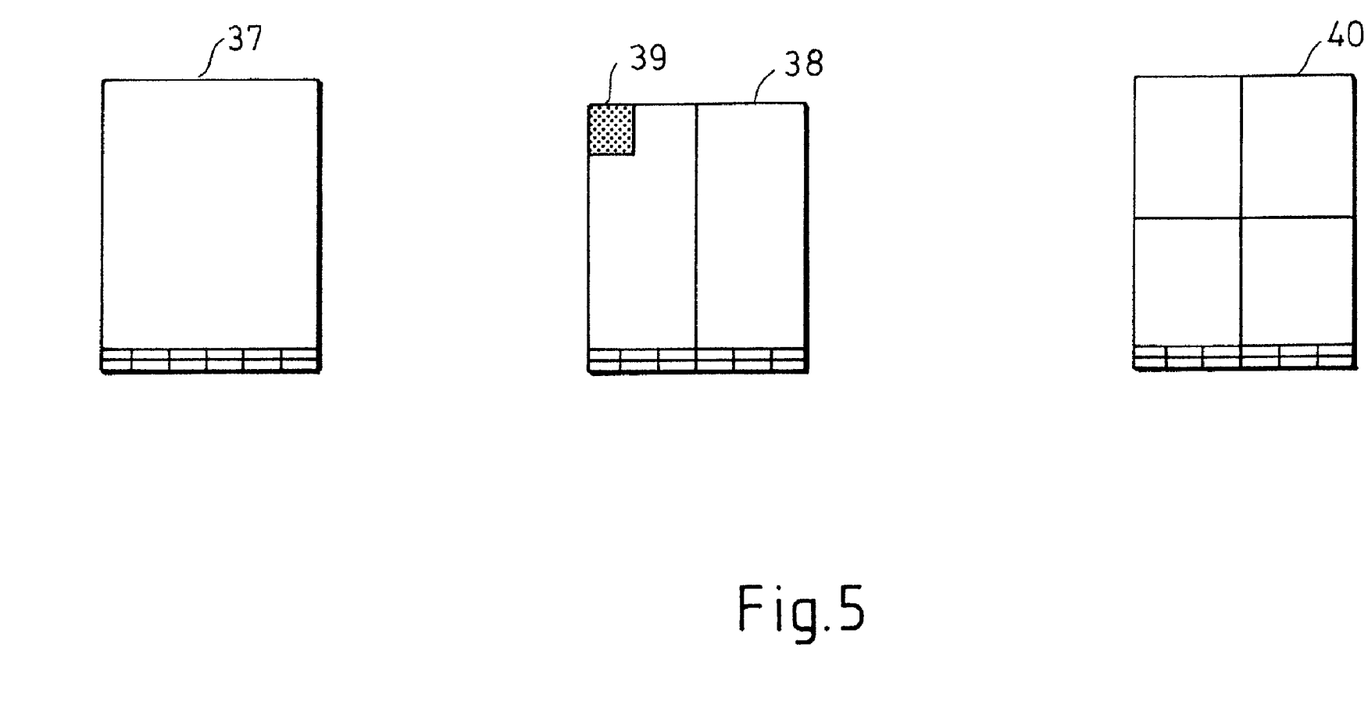
FIG. 5 shows various tilings of a single monitor embodiment.

FIG. 5 shows three different tilings of the display in a single monitor mode. The display 37 shows a single tiling and the display 38 a half tiling with a look-up table window 39. The look-up table window 39 can be used in order to change or adjust the brightness and/or the contrast of the image.

Further, FIG. 5 shows a display 40 with a quarter tiling. The quarter tiling enables displaying four different views at the same time.

Figure 6:
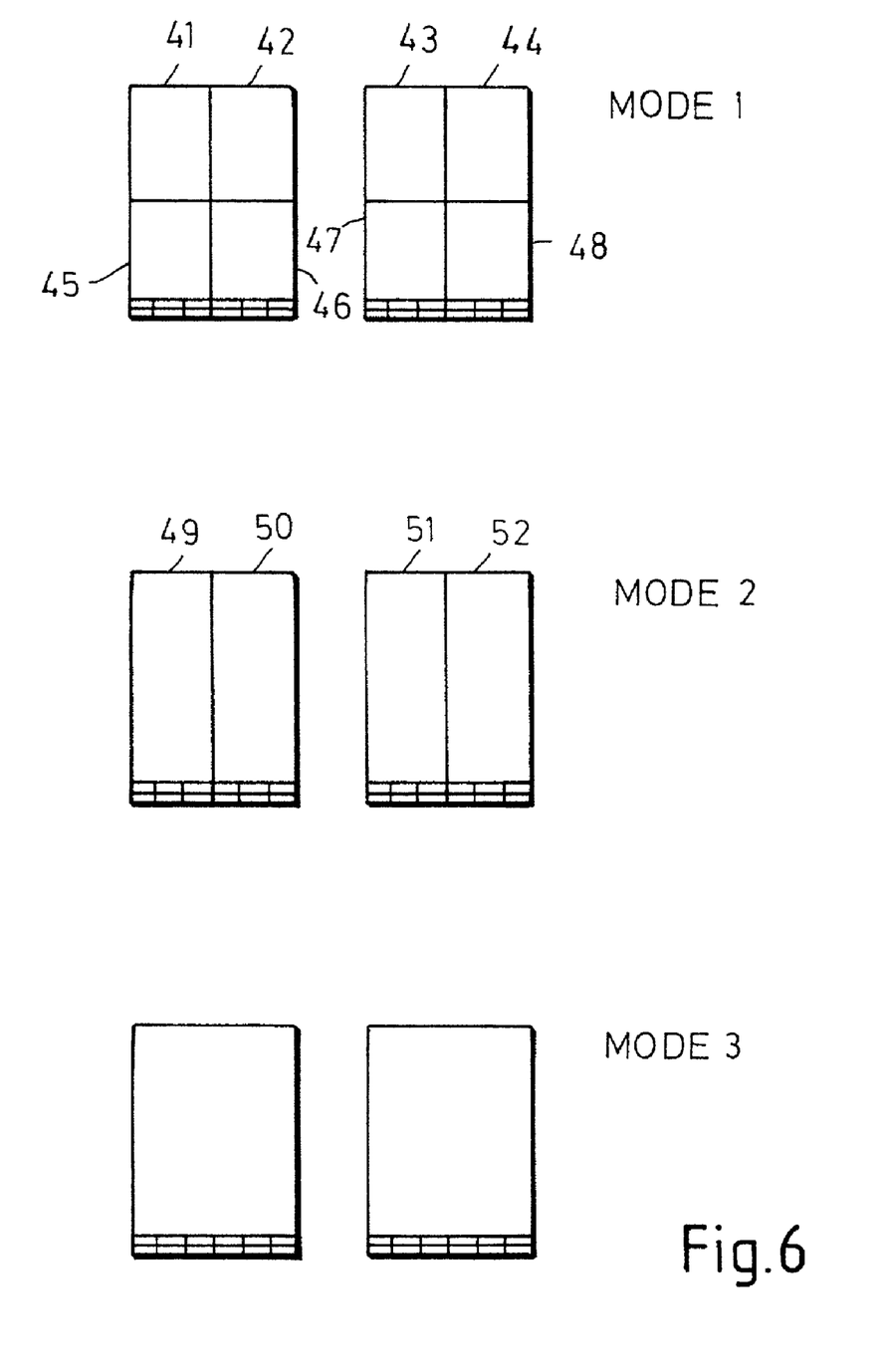
FIG. 6 shows various tilings of an embodiment with two monitors.

FIG. 6 shows corresponding display modes when using two monitors. The display mode 1 provides an overview for the radiologist. The tilings 41, 42, 43 and 44 can be used to display of prior images MLO right, MLO left, CC right, CC left. Likewise the tilings 45, 46, 47 and 48 of the lower row can be used to display the current images MLO right, MLO left, CC right and CC left, respectively of the current case.

In the display mode 2 there are tilings 49, 50, 51 and 52, as apparent from FIG. 6. These tilings allow an overview of a set of current or prior images.

In the display mode 3 the full screen of each monitor is used to display an image.

In order to specify a required image arrangement, the icons as listed in table 1 can be utilised. In order to specify a tool, a separate icon can be provided for each of the available functions as defined in respective rows of the table 2.

TABLE I

Overview image arrangement: 2 quarter tilings: maximum 8 images on two monitors. (upper row prior images: MLO right, MLO left (left monitor)/CC right, CC left (right monitor)) (lower row current images: MLO right, MLO left (left monitor)/CC right. CC left (right monitor))

Overview current image arrangement: 2 double tilings: maximum 4 images on two monitors. MLO right, MLO left (left monitor/CC right, CC left (right monitor)

Overview prior image arrangement: 2 double tilings: maximum 4 images on two monitors. MLO right, MLO left (left monitor)/CC right, CC left (right monitor)

MLO current (2 single tilings): right (left monitor)/left (right monitor)

MLO prior (2 single tilings): right (left monitor)/left (right monitor)

CC current (2 single tilings): right (left monitor)/left (right monitor)

CC prior (2 single tilings): right (left monitor)/left (right monitor)

MLO right (2 single tilings): prior (left monitor)/current (right monitor)

MLO left (2 single tilings): prior (left monitor)/current (right monitor)

CC right (2 single tilings): prior (left monitor)/current (right monitor)

CC left (2 single tilings); prior (left monitor)/current (right monitor)

Current right (2 single tilings): MLO (left monitor)/CC (right monitor)

TABLE I-continued

Current left (2 single tilings): MLO (left monitor)/CC (right monitor)

Prior right (2 single tilings): MLO (left monitor)/CC (right monitor)

Prior left (2 single tilings): MLO (left monitor)/CC (right monitor)

TABLE II

| | |
|---|---|
| CAD on | turns display of CAD results for all images of the current case on |
| CAD off | turns display of CAD results for all images of the current case off |
| ROAMING on | is only possible for single tilings displays the 50 micron images of the currently displayed images. The 50 micron images are larger than one monitor, so moving is needed to see all parts of the image |
| ROAMING off | is only possible for single tilings: changes the roaming images back into the single tilings. |
| CLAHE on | changes the currently displayed images into CLAHE images. |
| CLAHE off | changes the images of the current image arrangement back to original. |
| recycle | deletes the step |

Figure 7:
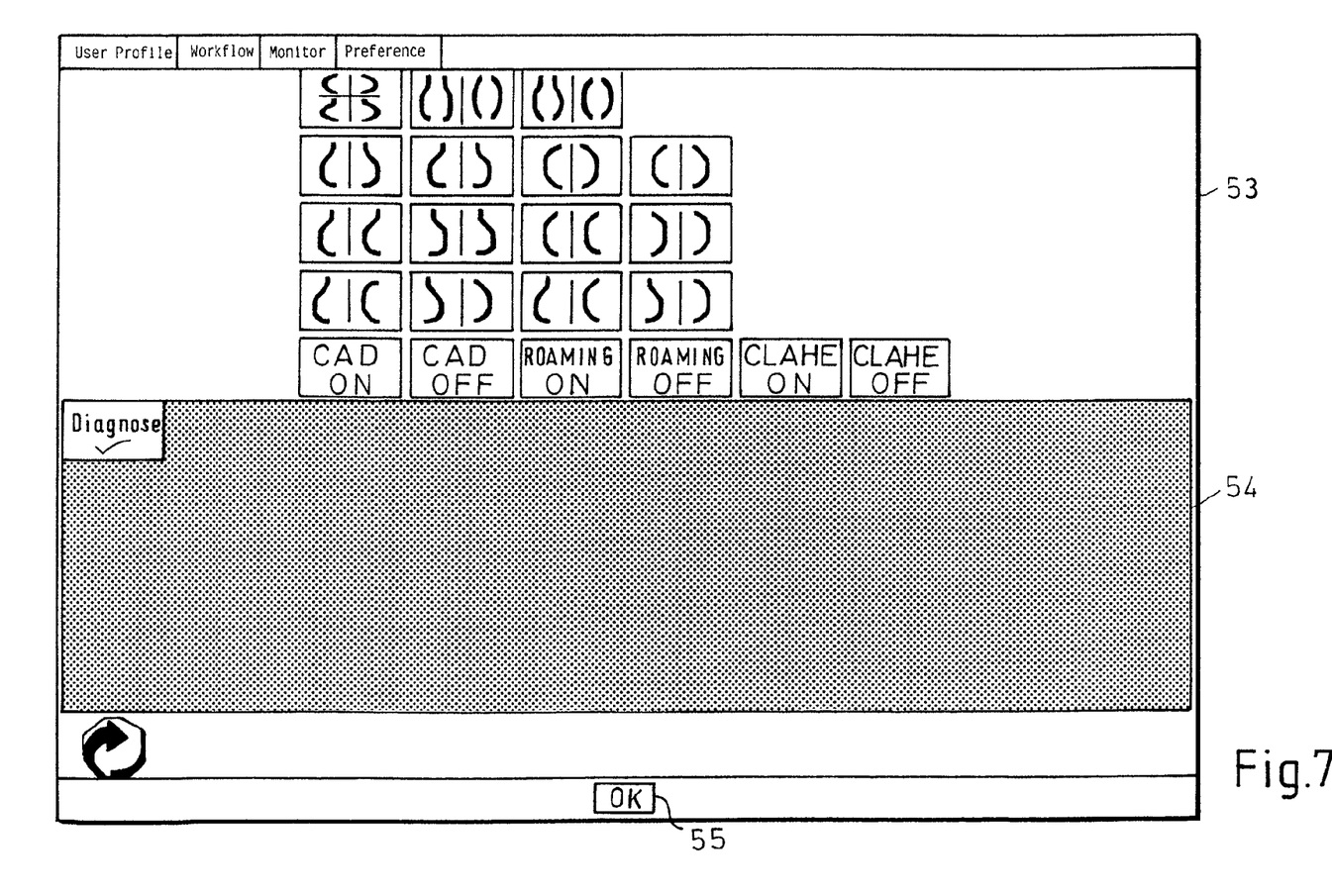
FIG. 7 is a further embodiment of the graphical user interface according to the invention.

FIG. 7 shows an embodiment of the graphical user interface in accordance with the invention which functions based on the icons as explained with respect to the tables 1 and 2. The graphical user interface contains a region 53 in which is shown all the icons that can be selected by a user for pre-programming the sequence of images. This is done by selecting one of the icons at a time and moving the selected icon to the region 54 that corresponds to the sequence bar 20 of FIG. 1. When the pre-programming is complete the user clicks on the OK button 55.

Figure 8:
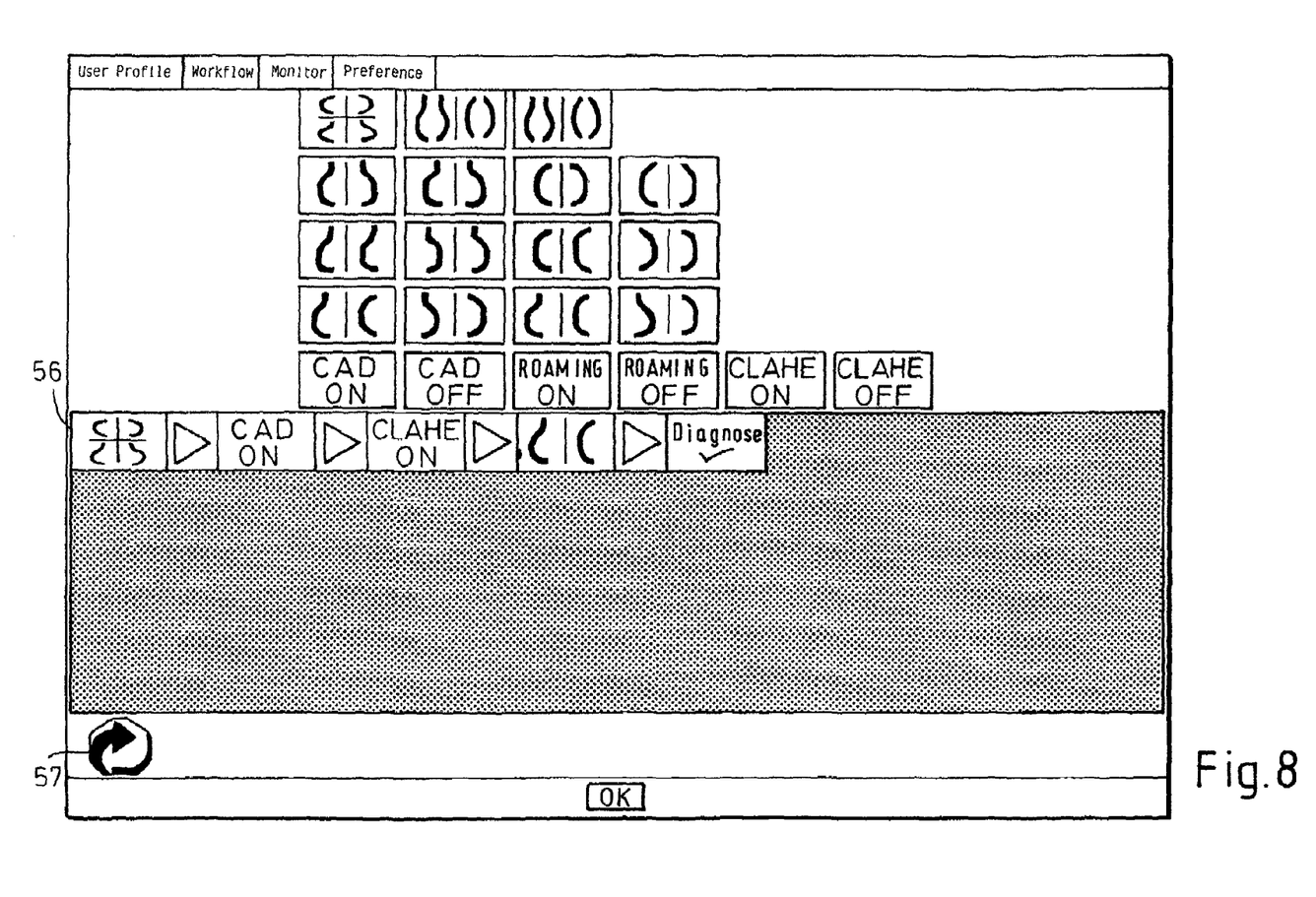
FIG. 8 illustrates the embodiment of FIG. 7 after the pre-programming of the sequence of images.

FIG. 8 shows the graphical user interface of FIG. 7 after a pre-programming has been performed. The resulting sequence of icons 56 is depicted in FIG. 8. The user can correct the sequence 56 by selecting an icon from the sequence 56 and moving the icon to the trash symbol 57.

Figure 9:
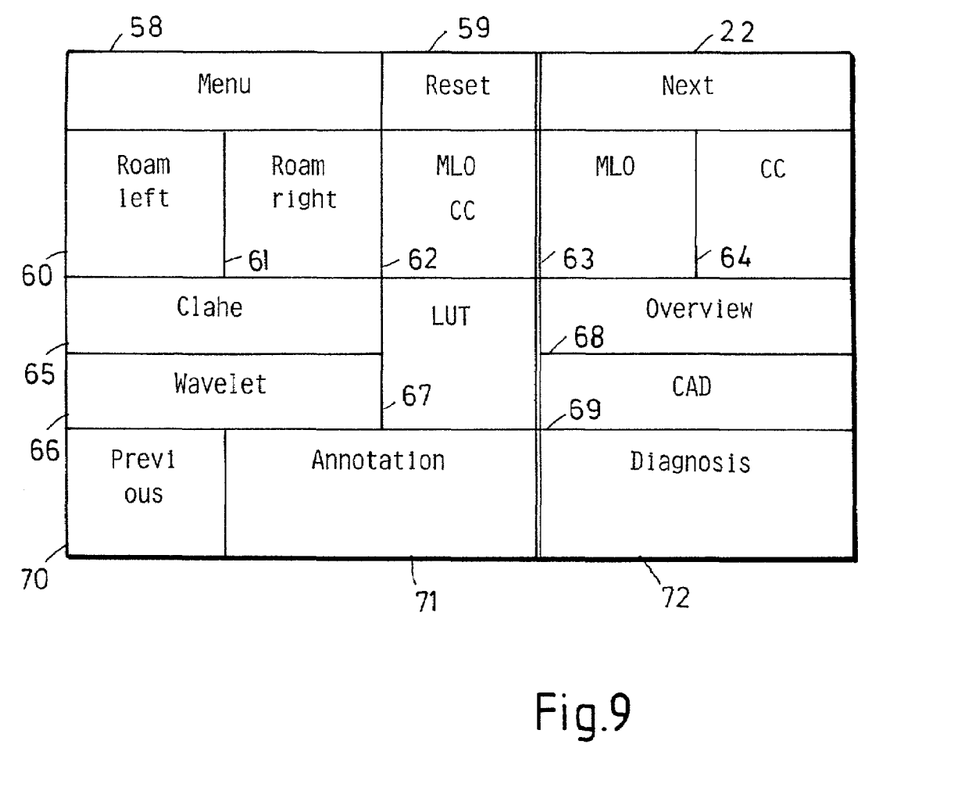
FIG. 9 shows an embodiment of a keypad for the user interface having a next-step button.

The FIG. 9 shows an example of a layout for the keypad 21. The keypad 21 has a next-step button 22 (cf. FIG. 1).

The menu button 58 serves to switch on and off the tool bars. The reset button 59 resets all tools and brings the computer system into the overview display mode.

The roaming left button 60 activates the roaming for the left monitor; the roaming right button 61 activates the roaming for the right monitor.

The MLO CC button 62 serves to select an overview current view in double tiling and the MLO button 63 serves to select a MLO current view.

The CC button 64 serves to select a CC current view. Pressing the CLAHE button 65 start a CLAHE enhancement for both monitors. The wavelet button 66 starts a wavelet enhancement for both monitors; the LUT button 67 serves to select the brightness/contrast mode as well as to deselect this mode.

The overview button 68 serves to select an overview of all images of a case with both monitors in quarter tiling. The CAD button 69 shows all CAD results for all images. The previous button 70 serves to go back to the preceding case; the annotation button 71 selects the annotation mode in order to highlight specific regions of interest in an image.

In response to pressing the diagnosis button 72, the diagnosis window is displayed in order to input a diagnosis for the current case. In response to pressing the diagnosis button 72 the computer system automatically goes to the consecutive case.

It is important to note that the buttons 22 and 58 to 72 of the keypads 21 are arranged such that the most frequently used buttons are located in an upper portion of the keypad 21. Lower buttons of the keypad 21 have decreasing degrees of importance in terms of their respective usage frequencies.

Although the present invention has been shown and described with respect to preferred embodiments, nevertheless, changes and modifications will be evident to those skilled in the art from the teachings of the invention. Such changes and modifications that embody the spirit, scope and teachings of the invention are deemed to fall within the purview of the invention as set forth in the appended claims.

List of Reference Numerals

| | |
|---|---|
| computer | 01 |
| graphical user interface | 02 |
| work flow memory | 03 |
| stack | 04 |
| pointer | 05 |
| memory | 06 |
| data field | 07 |
| data field | 08 |
| data field | 09 |
| data field | 10 |
| data field | 11 |
| pointer | 12 |
| IP module | 13 |
| retrieval module | 14 |
| display system | 15 |
| database | 16 |
| monitor | 17 |
| monitor | 18 |
| icons | 19 |
| sequence bar | 20 |
| keypad | 21 |
| next-step button | 22 |
| keyboard | 23 |
| mouse | 24 |
| mammogram | 25 |
| mammogram | 26 |
| display field | 27 |
| display field | 28 |
| display field | 29 |
| display field | 30 |
| toolbar | 31 |
| toolbar | 32 |
| region | 33 |
| region | 34 |
| region | 35 |
| region | 36 |
| display | 37 |
| display | 38 |
| look-up table window | 39 |
| display | 40 |
| tiling | 41 |
| tiling | 42 |
| tiling | 43 |
| tiling | 44 |
| tiling | 45 |
| tiling | 46 |
| tiling | 47 |
| tiling | 48 |

-continued

| | |
|---|---|
| tiling | 49 |
| tiling | 50 |
| tiling | 51 |
| tiling | 52 |
| region | 53 |
| region | 54 |
| ok-button | 55 |
| sequence | 56 |
| trash symbol | 57 |
| menu button | 58 |
| reset button | 59 |
| roaming left button | 60 |
| roaming right button | 61 |
| MLO space CC button | 62 |
| MLO button | 63 |
| CC button | 64 |
| CLAHE button | 65 |
| wavelet button | 66 |
| LUT button | 67 |
| overview button | 68 |
| CAD button | 69 |
| previous button | 70 |
| annotation button | 71 |
| diagnosis button | 72 |

What is claimed is:

1. A method for screening medical cases comprising the steps of:
   a.) storing a multiplicity of medical cases each of which contain a group of images of a particular portion of a patient's anatomy, the views of the images of all groups for all medical cases being the same;
   b.) establishing a preselected order of the medical cases;
   c.) providing a user interface with a set of icons, each individual icon representing a specification (i) for a designation of a particular view of an image of the group of images and (ii) for the processing thereof;
   d.) establishing a common workflow containing a plurality of serially arranged data fields;
   e.) interrelating the common workflow with the medical eases to screen orderly one by one;
   f.) preprogramming a sub-set of the set of icons into a preselected order corresponding to the serially arranged data fields of the common workflow by the user selecting the sub-set of icons and the order;
   g.) loading the specifications represented by the ordered sub-set of icons of the set of icons into the corresponding data fields of the common workflow;
   h.) coupling the user interface to the common workflow whereby a user can control stepping through the serial data fields;
   i.) in response to a user stepping to a data field, retrieving from the store of medical cases the specified particular view of an image of the current medical case being screened, processing as specified by the data field, and storing in the data field of the common workflow;
   j.) whereby an ordered sequence of preselected specified images of each medical case can be viewed, one by one, as derived from the stored groups of images for all said medical cases;
   k.) displaying, for viewing by a user, each ordered sequence of said preselected specified images derived from the stored images of each said medical case, in order, one after the other; and
   l.) controlling the stepping through the serially arranged data fields to view the ordered sequence of said preselected specified images derived from the stored images of each medical case by a user initiating only a single action input to move the workflow from each current serial data field to the next successive serial data field.

2. A method for screening medical cases according to claim 1 wherein each icon of the set of icons specifies one of an image, an image view, an image resulting from processing of an image according to a preselected algorithm, a tiling of images, activation of the marking of a region of interest, entry of a diagnosis, entry of an annotation, an image resulting from a computer aided diagnosis function performed on an image, and activation of the display of computer assisted diagnosis markers.

3. A method for screening medical cases according to claim 1 including the further step of providing a screen coupled to the user interface, displaying the set of icons on the screen, providing on the screen a sequence bar, and carrying out the preprogramming step f) by drag-and-drop of the icons on the sequence bar.

4. A method for screening medical cases according to claim 1 wherein the single action input of step I) is effected by one of pressing a key, touching a screen at a designated point, and speaking to a speech recognition component.

5. A method for screening medical cases according to claim 1 including the further step of highlighting an image being viewed by a graphical input tool included in the user interface.

6. A method for screening medical cases according to claim 1 including the further step of entering and storing an annotation for one of a medical case or an image being viewed.

7. A method for screening medical cases according to claim 1 including the further step of maintaining a stack of medical cases interrelated with the workflow.

8. A method for screening medical cases according to claim 1 including the further steps of storing the preprogrammed sub-set of the set of icons and storing a user ID.

9. A method for screening medical vases according to claim 1 including the further step of initiating via the user interface one of (i) editing the preprogramming and (ii) moving to the next medical case for viewing.

10. A method for screening medical cases according to claim 1 including the further step of providing an indication the medical case and specified image being currently viewed by a user.

11. Apparatus for screening medical cases comprising:
a) a store for storing a multiplicity of medical cases each of which contain a group of images of a particular portion of a patient's anatomy, the views of the images of all groups for all medical cases being the same;
b) means for establishing a preselected order of the medical cases;
c) a user interface with a set of icons, each individual icon representing a specification (i) for a designation of a particular view of an image of the group of images and (ii) for the processing thereof;
d) a common workflow containing a plurality of serially arranged data fields;
e) means for interrelating the common workflow with the medical eases to screen orderly one by one;
f) means for enabling a user to preprogram a sub-set of the set of icons into a preselected order corresponding to the serially arranged data fields of the common workflow by the user selecting the sub-set of icons and the order;
g) means for loading the specifications represented by the ordered sub-set of icons of the set of icons into the corresponding data fields of the common workflow;
h) the user interface being coupled to the common workflow to enable a user to control stepping through the serial data fields one after the other;
i) means, in response to the user actuating a single action input for stepping from a data field to the next successive data field, for retrieving from the store of medical cases, for each serial dais field, the specified particular view of an image of the current medical case being screened, for processing as specified by the data field, and for storing in the next successive data field of the common workflow;
j) whereby an ordered sequence of preselected specified images of each medical ease can be viewed, one by one, as derived from the stored groups of images for all said medical cases; and
k) a display for displaying, for viewing by a user, each ordered sequence of said preselected specifications of each said medical case, in order, one after the other.

12. Apparatus for screening medical cases according to claim 11 wherein each icon of the set of icons specifies one of an image, an image view, an image resulting from processing of an image according to a preselected algorithm, a tiling of images activation of the marking of a region of interest, entry of a diagnosis, entry of an annotation, an image resulting from a computer aided diagnosis function performed on an image, and activation of the display of computer assisted diagnosis markers.

13. Apparatus for screening medical cases according to claim 11 including a screen coupled to the user interface for displaying the set of icons on the screen, a sequence bar on the screen and whereby the preprogramming is carried out by drag-and-drop of the icons on the sequence bar.

14. Apparatus for screening medical cases according to claim 11 wherein the single action input is effected by one of pressing a key, touching a screen at a designated point, and speaking to a speech recognition component.

15. Apparatus for screening medical cases according to claim 11 including a graphical input tool included in the user interface for highlighting an image being viewed.

16. Apparatus for screening medical cases according to claim 11 including an annotation component for entering and storing an annotation for one of a medical case or an image being viewed.

17. Apparatus for screening medical cases according to claim 11 wherein the interrelationship between the common workflow and the medical eases is achieved via a stack.

18. Apparatus for screening medical eases according to claim 11 wherein the single action input is used to step from one medical case to the next succeeding medical case.

19. Apparatus for screening medical cases according to claim 11 wherein pointers are provided to indicate which medical case and which specified image of the ordered sequence of said preselected specified images is being currently viewed by a user.

* * * * *